United States Patent [19]

McLaurin-Smith

[11] Patent Number: 4,961,418
[45] Date of Patent: Oct. 9, 1990

[54] HEAT RETAINING FABRIC AND PHYSICAL THERAPY APPLIANCES

[76] Inventor: Mark McLaurin-Smith, 20/1 Carisle Close, North Ryde N.S.W., Australia, 2113

[21] Appl. No.: 363,401

[22] Filed: Jun. 5, 1989

Related U.S. Application Data

[63] Continuation of Ser. No. 30,894, Mar. 26, 1987, abandoned.

[51] Int. Cl.$^5$ .................. A61F 13/00; A61F 15/00
[52] U.S. Cl. ..................... 128/157; 128/165; 128/169; 128/77; 2/161 R; 2/164; 2/243 A; 428/507
[58] Field of Search .............. 128/75, 77, 78, 80 R, 128/80 C, 80 H, 155, 156, 157, 165, 169; 2/161 A, 161 R, 164, 167, 243 A, DIG. 1, DIG. 6, DIG. 7, 16; 26/2 R; 428/507

[56] References Cited

U.S. PATENT DOCUMENTS

| | | | |
|---|---|---|---|
| 2,717,437 | 9/1955 | De Mestral | 2/DIG. 6 |
| 2,787,266 | 4/1957 | Scholl | 128/156 |
| 3,092,110 | 6/1963 | Duensing | 128/293 |
| 3,613,681 | 10/1971 | Adams | 128/293 |
| 3,892,239 | 7/1975 | Masso Remiro | 128/293 |
| 4,084,586 | 4/1978 | Hettick | 128/157 |
| 4,121,582 | 10/1978 | Masso Remiro | 128/157 |
| 4,193,134 | 3/1980 | Hanrahan et al. | 2/16 |
| 4,350,726 | 9/1982 | Berry, Jr. | 428/316.6 |
| 4,414,970 | 11/1983 | Berry | 128/156 |
| 4,433,024 | 2/1984 | Eian | 428/198 |
| 4,622,908 | 11/1986 | Tranberg | 128/80 C |

FOREIGN PATENT DOCUMENTS

| | | | |
|---|---|---|---|
| 8101240 | 5/1981 | PCT Int'l Appl. | 128/165 |
| 0840523 | 7/1960 | United Kingdom | 128/165 |

OTHER PUBLICATIONS

Howley's Condensed Chemical Dictionary, 11th ed. Sax et al (editors), ©1987,1981,1971..., pp. 814–815.

Primary Examiner—Randall L. Green
Assistant Examiner—Paul Prebilic
Attorney, Agent, or Firm—Kilpatrick & Cody

[57] ABSTRACT

Physical therapy appliances for use in treatment of minor muscle, ligament, joint and similar injuries to promote healing and comfort during periods of both physical activity and physical inactivity comprising generally sleeve-like wraps of a heat-retaining composite material of resilient foam bonded between a single-jersey knit cover and a pile-surface inner knit fabric which stimulates the skin surface, wicks perspiration away from the skin surface and permits circulation of air adjacent to the skin surface beneath the foam layer.

3 Claims, 3 Drawing Sheets

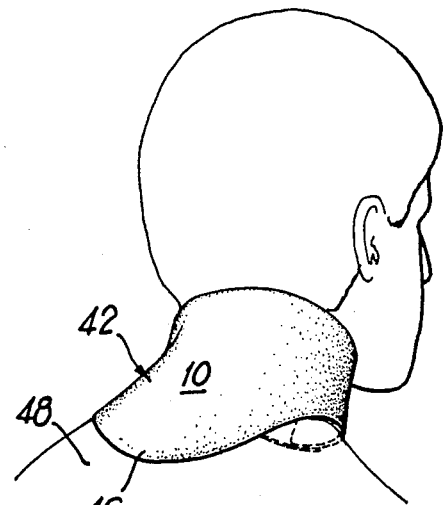
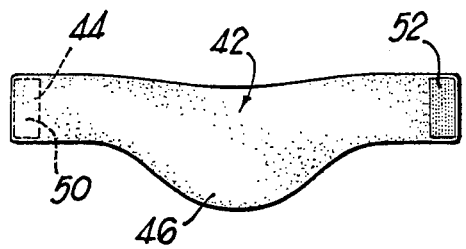
FIG 8   FIG 9
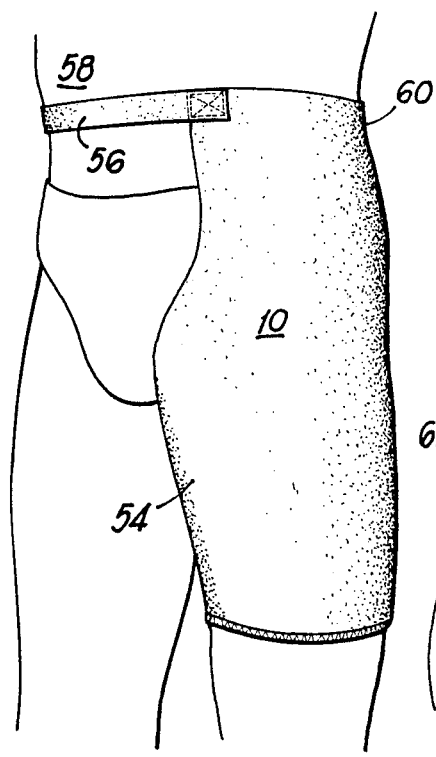
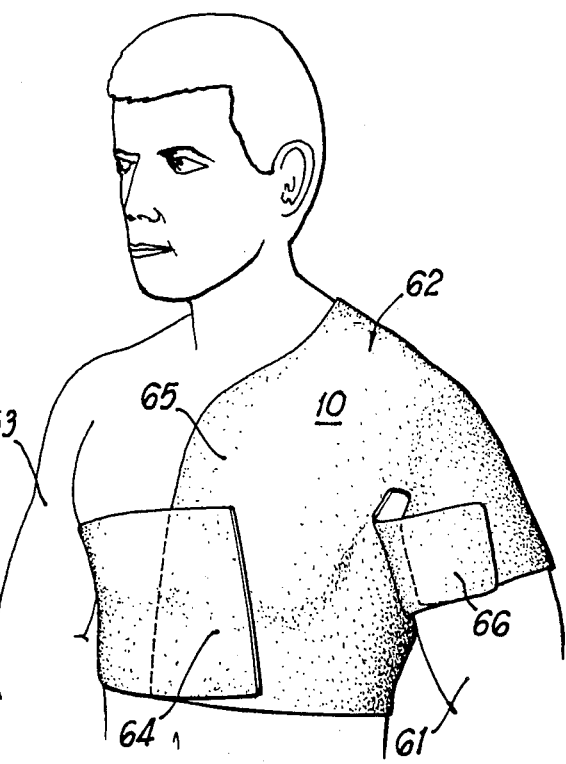
FIG 10   FIG 11

HEAT RETAINING FABRIC AND PHYSICAL THERAPY APPLIANCES

This is a continuation of an application for Heat Retaining Fabric and Physical Therapy Appliances, Ser. No. 030,894, filed on Mar. 26, 1987 now abandoned.

BACKGROUND OF THE INVENTION

This invention relates to composite fabric structures and physical therapy appliances, particularly those intended for human use.

Human injuries resulting from accidents and occupational and recreational physical activities are frequent. Such injuries and consequent pain frequently result from overloading, repetitive strain and other causes resulting in injuries to muscles, tendons, ligaments and other body tissue. Such injuries result not only in pain but also in the need to limit or eliminate physical activity involving the injured area, with resulting loss time and diminished work and recreational activities. Other animals, particularly including horses, also suffer similar injuries and consequent problems.

Conventional therapy for such injuries includes the application of elastic bandages to provide compression and, in some instances, limitation of movement. Other therapies include the application of cold packs, the application of heat, and immobilization of limbs or other affected areas.

Prior approaches to provision of therapeutic appliances for use on injured body areas include the following U.S. patents.

Patent No. 2,787,266, for a "Laminated Stretchable Cushion Material," issued to W. M. Scholl describes a material for use as an elastic surgical bandage formed by laminating fabric and porous foam latex.

Patent No. 3,092,110, for a "Muscular Thermal Support Sheath," issued to M. W. Duensing describes a heat retaining and supporting sheath made of fabric-lined rubber, such as foam rubber or foam neoprene. The lining is intended to absorb perspiration and protect the skin of a person who is allergic to contact with rubber or neoprene.

Patent No. 3,613,681 issued to J. R. Adams for a "Therapeutic Aid" discloses a closed cell, resilient, foamed elastomeric sheath with inner and outer isotonic surface coverings which may be knitted material.

Patent No. 3,892,239 for a "Quinohydrothermic Body Covering Element" to Masso Remiro describes a heat retaining stratified material which includes a thin layer of rubber with a laminar construction which decreases in section progressively in one direction. Both surfaces may be covered with knitted fabric, and the inner surface is crenelated. Patent No. 4,121,582 for "Direct Body Covering Sheet Having A Correcting And/Or Therapeutic Action," also issued to Masso Remiro, describes a fabricated sheet structure apparently substantially similar to that disclosed in patent number 3,892,239.

Patent No. 4,084,586 to Hettick, for a "Tubular Support for Enclosing a Body Member," describes an elastic, generally tubular appliance stretchable in all directions to provide gripping support and pressure to the surface of a body member which it encloses. The appliance is formed of a closed cell neoprene rubber layer with nylon knit material bonded to the inner and outer rubber surfaces to provide fabric surfaces which have a relatively low coefficient of friction.

Patent No. 4,414,970 for "Elastic Bandages" to Berry describes moisture vapor transmitting elastic bandages formed of an elastomeric film sandwiched between inner and outer fabric layers.

Patent No. 4,433,024 for "Reduced-Stress Vapor-Sorptive Garments" to Eian discloses a vapor-sorbing particle-filled sheet material having low insulation value for use in garments.

Many of the prior elastic bandages or elastic wraps are not anatomically correct to provide uniform compression and long-term comfort. Conventional heat sources are also deficient in that they frequently provide heat only for a limited period of time or, in the case of electric heating pads, limit user mobility and cannot be utilized while engaging in most other activities. Many conventional appliances utilized for therapy with the injuries described above are also unattractive and therefore unacceptable for wear and use in many situations. They also do not permit circulation of air adjacent to the skin, which results in retention of perspiration directly against the skin with consequent softening and wrinkling or maceration of the skin and lastitude of underlying muscle. Finally, prior wraps and appliances do not desirably stimulate the skin surface.

BRIEF DESCRIPTION OF THE INVENTION

The present invention overcomes these and other deficiencies of the prior art by providing a composite fabric structure and anatomically contoured appliances formed of that composite fabric to provide superior heat, compression and skin stimulation therapy appliances.

The composite fabric includes three layers. The outer layer is a conventional nylon single-jersey knit fabric which stretches in all directions and provides an attractive and protective covering. The inner layer, which directly contacts the user's skin, is a knitted nylon fabric with interwoven yarn to form a loop pile which contacts and stimulates the user's skin.

Sandwiched between the inner and outer fabric layers is a resilient foam layer of closed cell, light density copolymer (neoprene) polychloroprene. The fabric layers are bonded to the foam layer with glue.

The other fabric layer binds together and protects the appliance formed of the fabric of the present invention. The middle copolymer polychloroprene layer provides light compression to counteract tissue swelling and acts as an insulating layer to retain body heat within the inner layer and in the affected body area. The inner fabric layer also wicks perspiration away from the skin surface and holds that moisture. This keeps the skin surface itself relatively dry to reduce skin maceration and lastitude of underlying muscle. Because the nylon fiber utilized in the inner layer absorbs relatively little moisture, the fiber itself does not become saturated with perspiration as certain other fibers would, with resulting wearer discomfort. The open structure of the inner layer also retains a substantial quantity of air between the middle layer and the underlying skin, permitting that air to circulate, thereby ventilating the skin surface and consequently reducing excessive perspiration.

The resulting composite fabric of the present invention optimizes retention of body heat in the affected area and retains that heat with resulting therapeutic benefits. Importantly, skin surface stimulation results from contact and friction between the pile surface inner fabric layer and the skin surface, and such stimulation helps dialate the skin surface capillary beds to produce greater blood circulation. As a result of ventilation provided by the inner layer, the skin surface under the present invention remains comfortably dry during normal activity. During heavy activity, the area will perspire normally.

BRIEF DESCRIPTION OF THE DRAWINGS

FIG. 8 is a perspective view of a neck appliance in accordance with the present invention shown in place on a human neck.

FIG. 9 is a plan view of the neck appliance of FIG. 8 lying flat.

FIG. 10 is a perspective view of a groin and hip appliance in accordance with the present invention shown in place on a human groin and hip.

FIG. 11 is a perspective view of a shoulder appliance in accordance with the present invention shown in place on a human shoulder.

DETAILED DESCRIPTION OF THE DRAWINGS

As is illustrated in FIGS. 1, 5, 6, 7, 8, 9, 10 and 11, therapeutic appliances in accordance with the present invention are formed by fabricating sleeve-like wrappings which snuggly encircle injured areas of the body. This may be accomplished by sewing appropriately shaped sections of the composite material 10 of the present invention as described in more detail below.

Figure 1:
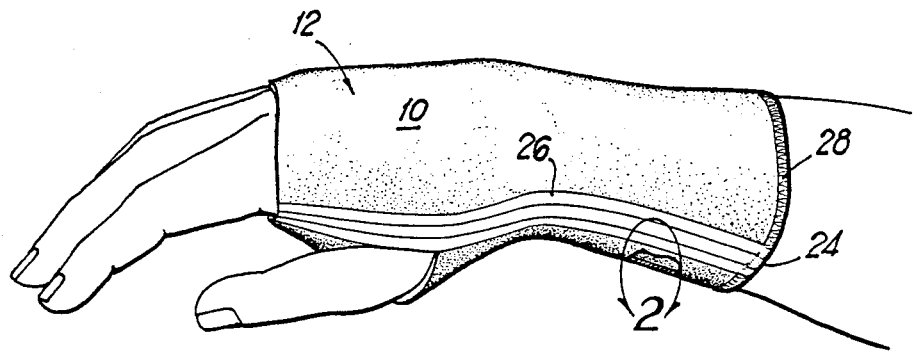
FIG. 1 is a perspective view of a hand and wrist therapeutic appliance of the present invention shown in place on a human hand.
Figure 2:
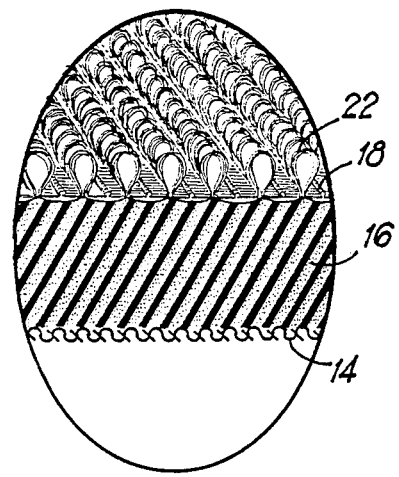
FIG. 2 is an enlarged schematic section view of the composite material of the present invention taken from oval 2 in FIG. 1.

FIG. 1 illustrates a wrist and hand appliance 12 in accordance with the present invention formed of such composite material 10. FIG. 2 is a partially schematic sectional view of composite material 10, which comprises generally a conventional nylon single-jersey knit fabric 14 bonded to one side of the foam layer 16 and an inner fabric 18 bonded to the other side of the foam layer 16. The inner fabric 18 contacts the skin 20 of a user of an appliance 12 fabricated from composite material 10.

Figure 3:
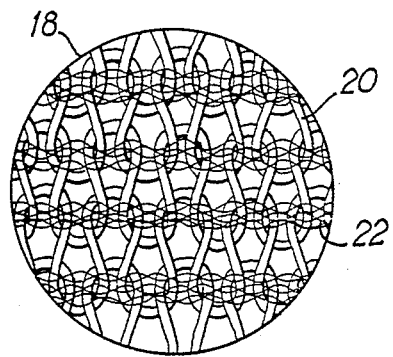
FIG. 3 is an enlarged schematic view of the inside fabric layer of the composite material of the present invention.
Figure 4:
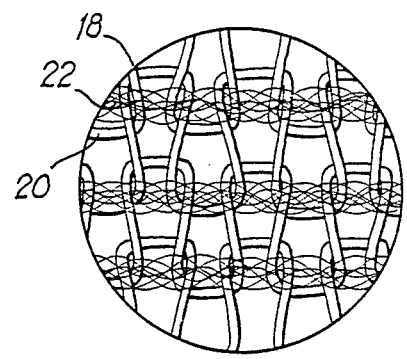
FIG. 4 is an enlarged schematic view substantially similar to FIG. 3 showing the fabric stretched in all directions.
Figure 5:
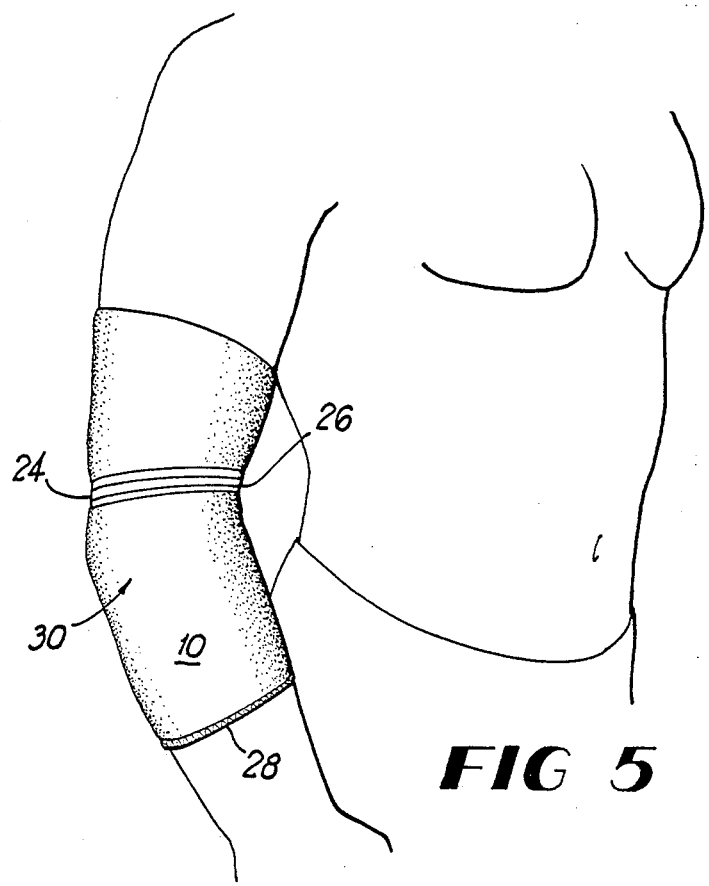
FIG. 5 is a perspective view of an elbow appliance in accordance with the present invention shown in place on a human elbow.

Inner fabric layer 18 is further illustrated in a relaxed condition in FIG. 3 and stretched in FIG. 4. As is schematically illustrated in FIG. 3, inner fabric layer 18 is a nylon fabric produced on a circular knitting machine utilizing a weft knitting technique. The preferred fabric layer 18 is produced on a twenty (20) guage circular knit weft knitting machine with number two (2) height sinkers utilizing yarn which is seventy-five percent (75%) tri lobal nylon fiber, one hundred-fifty (150) denier, seventy-five (75) filament, and twenty-five percent (25%) nylon fiber, seventy-eight degrees (78) denier, twenty (20) filament. As is illustrated in FIGS. 3 and 4, fabric layer 18 includes a knitted fabric base 20 which is substantially the seventy-eight degrees (78) denier, twenty (20) filament yarn described above. Yarn 22, which is the tri lobal nylon fiber (150 denier, 75 filament), protrudes from the surface of inner fabric layer 18 to promote skin surface stimulation as a result of friction and contact between the inner fabric layer 18 and the skin surface 20, which helps dialate the skin surface capillary beds to produce greater blood circulation. Because of the substantial air space within the structure of inner fabric 18, the skin 20 under the present invention remains comfortably dry during normal activity, and air can circulate adjacent to skin 20.

The outer jersey knit layer 14 may be any conventional fabric which provides a pleasant appearance, will stretch in all directions, and provides a cover for the appliance 12. A suitable fabric is a conventional nylon single-jersey knit fabric knitted from seventy-eight (78) denier, twenty (20) filament nylon yarn. Outer layer 14 might even be omitted entirely if foam layer 16 is provided with outer appropriate protection such as a suitable polymeric layer or coating.

The foam layer 16 of the present invention may be a resilient foam formed of a closed-cell, light density copolymer (neoprene) polychloroprene. Suitable foam 16 for use in forming the composite material 10 of the present invention may be obtained from Akti Industries Pty., Ltd., 3 Governor Road, Braeside, Melbourne, Victoria, Australia.

Each of the inner fabric layer 14 and the outer fabric layer 18 is bonded to foam layer 16 utilizing a two-step process. A hydraulic, dual-roller pressing machine is utilized to apply glue and fabric simultaneously to the foam, and a hydraulic heat press is then used to cure the glue. Suitable glue is Super Bond Adhesive, grade S 758, which may be obtained from Thomas Stewart & Co. Pty. Ltd., 5 Marsh Street, Granville, New South Wales, Australia.

An appliance such as wrist and hand wrap 12 may be formed in accordance with the present invention as follows. A suitably shaped section of composite material 10 is cut and then formed into a generally sleeve-like or tube-like shape as is illustrated in FIG. 1, by joining opposite edges of composite material 10 with a seam 24 by any conventional appropriate sewing technique, including the use of an appropriate binding tape 26. Exposed edges of composite material 10 may be bound by any appropriate technique which does not unduly limit the natural stretch characteristics of composite material 10 as, for instance, by overstitching 28 illustrated in FIGS. 1, 5, 6 and 7. Bending lines in composite material 10 may be provided utilizing seams and seam binding tape as is illustrated by seam 24 and binding tape 26 which forms a bending line 40 in the elbow appliance of the present invention illustrated in FIG. 5.

Figures 6, 7:
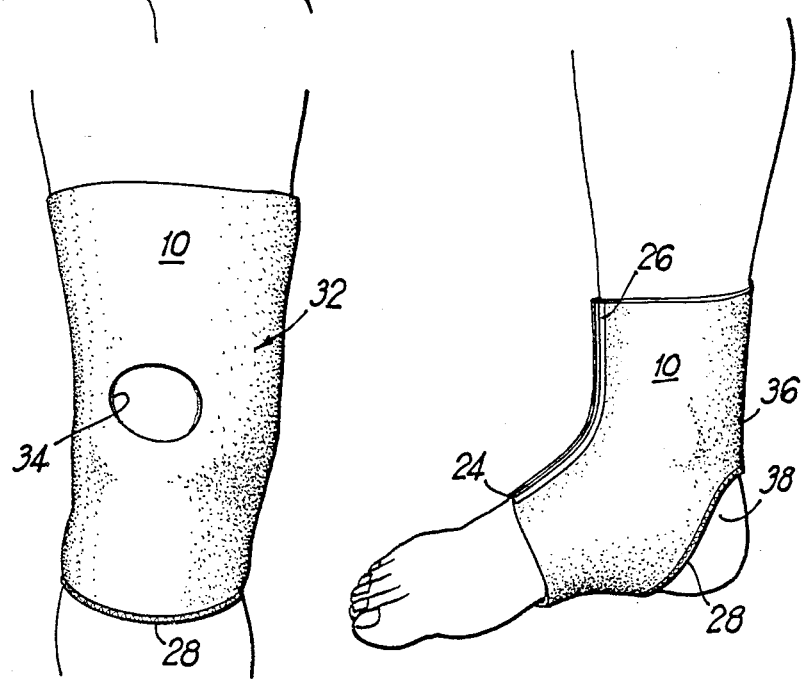
FIG. 6 is a perspective view of a knee appliance with a kneecap cutout in accordance with the present invention shown in place on a human knee.
FIG. 7 is a perspective view of an ankle appliance in accordance with the present invention shown in place on a human ankle.

Additionally, appropriate cutouts may be provided to expose portions of the anatomy which it is not desired to cover with continuous sections of composite material 10. Such cutouts are illustrated in FIGS. 6 and 7. FIG. 6 illustrates a knee appliance 32 having kneecap cutout 34, and FIG. 7 illustrates ankle appliance 36 having a heel cutout 38.

FIGS. 8 and 9 illustrate a neck appliance 42 constructed of the composite material 10 of the present invention by forming a section of material 10 into an elongated, generally rectangular strip 44 with an arcuate depending region 46 which, in use, extends generally down the wearer's back 40.

Neck appliance 42 may be snugly fitted in place by the wearer by overlapping the ends of strip 44 generally under the wearer's chin and fastening them with any suitable fastening means such as hook and loop fasteners 50 and 52.

FIG. 10 shows a groin and hip appliance 54 formed of composite material 10 in accordance with the present invention. Such an appliance 54 may be constructed by forming composite material 10 into a tapered tube having the general shape of the upper portion of one trousers leg. A waist band 56 encircles the wearer's waist 58 and attaches to the upper margin 60 of appliance 54 in order to support appliance 54 and hold it in place on the wearer. Waist band 56 may be closed by any suitable fastener such as hook and loop material. As will be appreciated by reference to FIG. 10, a groin and hip appliance 54 so constructed provides the light compression, heat retention and skin surface stimulation and other benefits of the present invention to the upper thigh, groin and hip areas of one side of a user's body.

FIG. 11 illustrates a left shoulder appliance 62 constructed of composite material 10 of the present invention by forming a snuggly fitted appliance 62 having the general shape of the shoulder area of the left side of a conventional shirt or jacket. Composite material 10 is formed to overlie the wearer's shoulder and upper left arm 61, and a large chest flap of composite material 10 extends from the back of shoulder appliance 62 around the wearer's side under the right arm 63 to overlie the wearer's chest and fasten to the front 65 of shoulder appliance 62 with any appropriate conventional fastening means such as hook and loop material. An arm flap 66 is formed by a portion of composite material 10 which extends around the back and inside of the wearer's left arm 61 below the armpit to encircle and fasten around the upper left arm 61, again utilizing hook and loop or other appropriate fastening means. As will be appreciated by reference to FIG. 11, the shoulder appliance 62 of the present invention also provides the compression, heat-retention, skin surface stimulation and other benefits of the present invention by snuggly overlying and encircling one shoulder and adjacent areas of a wearer. As will be readily apparent by reference to the preceding description, the benefits of therapeutic appliances formed of the composite material 10 of the present invention may be achieved by appropriately forming such fabric to conform to virtually any portion of the human anatomy. Such appliances may be manufactured to be utilized on other parts of the anatomy than those illustrated, including, for instance, the human back, calf, wrist and thigh, and a horse's knee or ankle. As will be appreciated by one skilled in the art, and by reference to the appliances illustrated in FIGS. 8-11, some of such appliances can best be positioned utilizing appropriate conventional closures such as hook and loop closures, buttons, zippers or the like. Additional appliance shapes which may be formed of the composite material 10 of the present invention include those shapes illustrated in U.S. Pat. No. 4,084,586 to Hettick and U.S. Pat. No. 3,613,681 to Adams, both of which are incorporated herein by this reference.

As will also be readily appreciated by one skilled in the art, appliances in accordance with the present invention can be fabricated in numerous forms in accordance with the foregoing disclosure and the accompanying drawings. The disclosure and drawings are intended to be merely illustrative of the invention and numerous additional embodiments of the invention can be practiced in accordance with the spirit of this disclosure without limiting the following claims.

I claim:

1. A therapeutic appliance for use against a skin surface on an injured portion of a human body to provide light compression, retain body heat and stimulate the skin surface, comprising a section of composite material formed to lie against and lightly compress the body portion, the composite material comprising an insulative resilient closed-cell foam layer, an inner stretchable fabric of hydrophobic fiber with a pile surface bonded to a first side of the foam layer and an outer stretchable cover bonded to a second side of the foam layer, the inner surface being of a weft knit of seventy-five percent tri lobal nylon fiber, one hundred-fifty denier, seventy-five filament and twenty-five percent nylon fiber, seventy-eight denier, twenty filament knitted on a twenty gauge circular knit weft knitted machine with number two height sinkers.

2. An appliance according to claim 1, wherein the body portion is a wrist and the section is formed into a tapered tube.

3. An appliance according to claim 1, wherein the body portion is a wrist and hand and the section is formed into a tube-shaped wrap with a wrist-hugging constriction and a thumb cut-out.

* * * * *